US008007831B2

(12) United States Patent
Lewis et al.

(10) Patent No.: US 8,007,831 B2
(45) Date of Patent: Aug. 30, 2011

(54) LOADING OF HYDROPHOBIC DRUGS INTO HYDROPHILIC POLYMER DELIVERY SYSTEMS

(75) Inventors: Andrew Lennard Lewis, Surrey (GB); Yiqing Tang, Surrey (GB); Maria Victoria Gonzalez Fajardo, Surrey (GB)

(73) Assignee: Biocompatibles UK Limited, Surrey (GB)

( * ) Notice: Subject to any disclaimer, the term of this patent is extended or adjusted under 35 U.S.C. 154(b) by 343 days.

(21) Appl. No.: 12/278,827

(22) PCT Filed: Feb. 9, 2007

(86) PCT No.: PCT/JP2007/051299
§ 371 (c)(1), (2), (4) Date: Aug. 8, 2008

(87) PCT Pub. No.: WO2007/090897
PCT Pub. Date: Aug. 16, 2007

(65) Prior Publication Data

US 2010/0166876 A1 Jul. 1, 2010

(30) Foreign Application Priority Data

Feb. 10, 2006 (EP) .................................... 06250742

(51) Int. Cl.

| | |
|---|---|
| ***A61K 9/16*** | (2006.01) |
| ***A61K 31/436*** | (2006.01) |
| ***A61K 31/337*** | (2006.01) |
| ***A61K 35/00*** | (2006.01) |
| ***A61K 31/573*** | (2006.01) |
| ***A61K 31/192*** | (2006.01) |
| ***B01J 13/04*** | (2006.01) |

(52) U.S. Cl. ........ 424/501; 514/291; 514/449; 514/180; 514/570; 264/4.33

(58) Field of Classification Search .................. 424/501
See application file for complete search history.

(56) References Cited

U.S. PATENT DOCUMENTS

| | | | | |
|---|---|---|---|---|
| 5,270,354 | A * | 12/1993 | Vermeersch et al. | 523/334 |
| 5,508,060 | A | 4/1996 | Perman et al. | |
| 6,214,387 | B1 | 4/2001 | Berde et al. | |
| 7,001,616 | B2 * | 2/2006 | Batich et al. | 424/489 |
| 2003/0202936 | A1 | 10/2003 | Batich et al. | |
| 2004/0071768 | A1 | 4/2004 | Sarris et al. | |
| 2005/0163914 | A1 * | 7/2005 | Klee et al. | 427/2.24 |

FOREIGN PATENT DOCUMENTS

| | | | |
|---|---|---|---|
| WO | 98/17256 | A1 | 4/1998 |
| WO | WO 2004/073688 | * | 2/2004 |

OTHER PUBLICATIONS

Vandelli et al. Microwave Treated Gelatin Microspheres as Drug Delivery System. Journal of Controlled Release, vol. 96. 2004.*
Vandelli et al. Microwave-treated gelatin microspheres as drug deliver system, Journal of Controlled Release, vol. 96, 2004.*
Maria Angela Vandelli et al., "Microwave-treated gelatin microspheres as drug delivery system", Journal of Controlled Release, vol. 96 (2004), pp. 67-84.

* cited by examiner

*Primary Examiner* — Shanon A Foley
*Assistant Examiner* — Sarah Al-Awadi
(74) *Attorney, Agent, or Firm* — Sughrue Mion, PLLC

(57) ABSTRACT

A process is described for loading hydrophilic polymer particles with a water-insoluble solvent-soluble drug. The particles are preferably embolic agents. The method provides particles having little or no drug at the surface and in a surface layer, whereby the burst effect is minimised. The drug is precipitated in the core of the particle, leading to extended release. The drug is, for instance, paclitaxel, rapamycin, dexamethasone or ibuprofen.

19 Claims, 7 Drawing Sheets

7A 7B 7C 7D

LOADING OF HYDROPHOBIC DRUGS INTO HYDROPHILIC POLYMER DELIVERY SYSTEMS

The present invention relates to methods for preparing hydrophobic drug loaded hydrophilic microspheres, having a non-burst and sustained release local delivery of drug at the site of embolisation.

Embolisation therapy involves the introduction of an agent into the vasculature in order to bring about the deliberate blockage of a particular vessel. This type of therapy is particularly useful for blocking abnormal connections between arteries and veins (such as arteriovenous malformations, or AVMs), and also for occluding vessels that feed certain hyper-vascularised tumours, in order to starve the abnormal tissue and bring about tumour ischemia or necrosis.

The process of embolisation may induce tumour necrosis or ischemia depending upon the extent of the embolisation. The response of the tumour cells to the hypoxic environment can result in an ensuing angiogenesis in which new blood vessels are grown to compensate for the loss of flow to the tumour by the embolisation. It would be desirable therefore to combine embolisation with the administration of agents that could prevent the ensuing angiogenic response or combine with the release of a cytotoxic or other anti-tumoral agent to bring about cell death in those cells that are not killed by the embolisation.

In the early 1960s, the National Cancer Institute (NCI) in the United States initiated a programme of biological screening of extracts taken from a wide variety of natural sources. One of these extracts was found to exhibit marked antitumour activity against a broad range of rodent tumours. Although this discovery was made in 1962, it was not until five years later that two researchers, Wall and Wani, of the Research Triangle Institute, North Carolina, isolated the active compound, from the bark of the Pacific yew tree (*Taxus brevifolia*). In 1971, Wall and Wani published the structure of this promising new anti-cancer lead compound, a complex polyoxygenated, Wani, M. C., H. L. Taylor, Monroe Wall, P. Coggon, A. T. McPhail, 1971, "Plant Antitumor Agents. VI. The Isolation and Structure of Taxol, a Novel Antileukemic and Antitumor Agent from *Taxus brevifolia*," Journal of the American Chemical Society, 93: 2325-2327.

Paclitaxel is a natural product with antitumor activity. It is used to treat ovarian cancer, Karposi's sarcoma, and used in combinations with other chemotherapy agents to treat breast cancer, non-small cell lung cancer and is most effective against ovarian carcinomas and advanced breast carcinomas. Paclitaxel is given intravenously (it irritates skin and mucous membranes on contact). Paclitaxel, which is sold as Taxol® by Bristol-Myers Squibb, is obtained via a semi-synthetic process from *Taxus baccata*. The chemical name is 5β,20-Epoxy-1,2α,4,7β,10β,13α-hexahydroxytax-11-en-9-one 4,10-diacetate 2-benzoate 13-ester with (2R,3S)—N-benzoyl-3-phenylisoserine. Paclitaxel is a white to off-white crystalline powder with the empirical formula $CH_{47}H_{51}NO_{14}$ and a molecular weight of 853.9. Paclitaxel is highly lipophilic, insoluble in water, and melts at around 216-217° C.

The relatively non-toxic properties of paclitaxel have made it a leading light in the treatment of cancer in the 1990s, providing a non-intrusive alternative to the more radical techniques of radiotherapy and surgery.

Despite its well-documented biological activity, very little interest was shown in paclitaxel until scientists at the Albert Einstein Medical College reported that its mode of action was totally unique. Until this finding in 1980, it was believed that the cytotoxic properties of paclitaxel were due to its ability to destabilise microtubules, important structures involved in cell division (mitosis). In fact, paclitaxel was found to induce the assembly of tubulin into microtubules, and more importantly, that the drug actually stabilises them to the extent that mitosis is disrupted. Such a novel mode of action was believed to make paclitaxel a prototype for a new class of anticancer drugs. Paclitaxel binds to microtubules and inhibits their depolymerization (molecular disassembly) into tubulin. It blocks a cell's ability to break down the mitotic spindle during mitosis (cell division). With the spindle still in place the cell cannot divide into daughter cells (this is in contrast to drugs like colchicine and the Vinca alkaloids, which block mitosis by keeping the spindle from being formed in the first place).

Most of the reported work on the preparation of paclitaxel-loaded polymeric drug delivery systems is based on hydrophobic polymer systems in which paclitaxel has good solubility.

WO2003/077967 relates to a deposition method for applying an active substance to an endoprosthesis having a thin polymer coating. The deposition method enables a slow and largely constant administering of an active substance, as cited in the example of tretinoin. Since additional processing steps are not required after the application of the active substance(s), it is unnecessary to worry about coating conditions causing the active substance to be broken down, for example, by the application of second polymer coating. Even relatively unstable active substances, e.g. tretinoin, can be applied without any difficulties to the endoprosthesis. Thus 4-amino-[2,2]-paracyclophane was cleaved at 700° C., 20 Pa to reactive monomers and polymerised at the surface of a stent at 20° C. The polymer-coated stent was contacted with a DMSO solution of tretinoin and dipped into water; this resulted the precipitation of tretinoin onto the surface of the stent and embedding of the precipitate into the polymer layer.

Angiotech's group have studied the paclitaxel loading into poly(L-lactic acid) (PLLA) microspheres using solvent evaporation method. PLLA and paclitaxel were dissolved in dichloromethane. The organic phase was added to an aqueous solution of 2.5% poly(vinyl alcohol) under stirring. Subsequently, after 2 hr the aqueous suspension containing microspheres was passed through sieves to retain the particles in certain size ranges. The microspheres were further dried for 12-16 hr at ambient temperature. [Richard T. Liggins, Helen M. Burt 'Paclitaxel loaded poly(L-lactic acid microspheres: properties of microspheres made with low molecular weight polymers' International Journal of Pharmaceutics 222 (2001) 19-33; Richard T. Liggins, Helen M. Burt 'Paclitaxel loaded poly(L-lactic acid) microspheres II. The effect of processing parameters on microsphere morphology and drug release kinetics' International Journal of Pharmaceutics 281 (2004) 103-106.] Later they extended their work on poly(lactic-co-glycolic acid) films for delivery of paclitaxel. [John K. Jackson, et al. 'Characterization of perivascular poly(lactic-co-glycolic acid] films containing paclitaxel' International Journal of Pharmaceutics 283 (2004) 97-109.] Other work includes PEG-coated poly(lactic acid) microspheres. [Gladwin S. Das, et al. 'Controlled delivery of taxol from poly (ethylene glycol)-coated poly(lactic acid) microspheres' Journal of Biomedical Materials Research 55 (2001) 96-103].

Boston Scientific Corporation has developed the system of coronary stent coating for delivery of paclitaxel by formulating polymer blends with 10 to 25% of paclitaxel. The polymers used are poly(butyl methacrylate), poly(styrene-co-isobutylene-co-styrene), or poly(styrene-co-(ethylene-butylene)-co-styrene), which are blended with poly(styrene-co-maleic anhydride). A recent development uses a modified styrenic portion, i.e. hydroxystyrene or its acetylated version. [Shrirang Ranade, et al. Abstracts of papers, 229th ACS national Meeting, San Diego, Calif., US, Mar. 13-17, 2005, PMSE-022].

Composition and methods for in vivo controlled release of pharmaceutically active agents associated with hydroxyapatite (HAP) in a pharmaceutically acceptable carrier are described in WO2003030943. The pharmaceutically acceptable carrier can be a polymer paste or gel which may contain a second pharmacologically active agent. Methods of making and administering controlled release compositions for the delivery of a pharmacologically active agent, such as a nucleic acid, in combination with a polycationic polymer and in a pharmaceutically acceptable carrier, to a mammal in a pharmaceutically effective amount are provided.

Rapamycin, also known as sirolimus, was isolated the first time in 1969 from a fungus (*Streptomyces hygroscopicus*) in the island of Rapa Nui (Easter Island). Initially it was found to have potent antifungal and antiproliferative activities; but it was in 1977 when Martel et al reported its promising immunosuppressive activity [Martel, R. R.; Canadian Journal of Physiological Pharmacology, 55, 48-51 (1977).] From this time its mechanism of action has been thoroughly studied, and it is known how this antibiotic exerts its immunosuppressive and antiproliferative activities. Rapamycin is a white to off-white powder and is insoluble in water, but freely soluble in benzyl alcohol, chloroform, acetone, and acetonitrile.

Rapamycin and rapamycin analogues are currently in clinical development against a number of cancer indications. The mechanism of action is as an inhibitor of the mammalian target of rapamycin (mTOR). The cyclic macrolide structure inhibits cellular proliferation by interfering with the highly conserved TOR pathway, which control the synthesis of essential proteins involved in cell cycle progression.

mTOR is a protein kinase with similarities to the catalytic domains of phosphoinositide 3-kinases (PI3-k). Once activated, TOR transduces signals that initiate synthesis of ribosomal proteins, translation of specific mRNAs and generation of cyclin-dependent kinases, promoting the progression of the cell cycle. This results in activation and proliferation of T and B-cells and antibody production as well as proliferation of non-immune cells such as hepatocytes, fibroblasts, endothelial cells and smooth muscle cells. [Neuhaus P, Klupp J, Langrehr J M.; Liver Transpl. 2001 June; 7(6):473-84. mTOR inhibitors: an overview.]

Rapamycin exerts its antiproliferative effect mainly by blocking all of these events, as a consequence of inhibition of mTOR. It is able to inhibit this protein kinase by forming a trimeric stable complex, after binding with the soluble intracellular receptor protein FKBP12. This inhibition blocks the synthesis of cyclin-dependent kinases, which are key mRNAs that code for proteins required for cell cycle progression from G1 to S phase.

mTOR is also a positive regulator of hypoxia-inducible factor-1-dependent gene transcription in cells exposed to hypoxia or hypoxia mimetic agents [Hudson C C, Liu M, Chiang G G, Otterness D M, Loomis D C, Kaper F, Giaccia A J, Abraham R T.; Mol Cell Biol. 2002 October; 22(20):7004-14. Regulation of hypoxia-inducible factor 1alpha expression and function by the mammalian target of rapamycin.] If rapamycins prove to be effective inhibitors of hypoxic adaptation in developing tumours, these drugs could have dramatic effects on tumour growth, invasiveness and metastatic potential in cancer patients. In embolisation a hypoxic environment is induced and therefore rapamycin and its analogues may act mechanistically by inhibiting mTOR and consequently inhibiting the production of hypoxia induced factor (HIF-1) widely believed to be involved in angiogenic responses.

Treatment of tumour-bearing animals with rapamycin results in decreased expression of VEGF mRNA and decreased circulating levels of VEGF protein. Thus, proliferation of smooth muscle and endothelial cells is inhibited by mTOR inhibition. This anti-angiogenic effect may contribute to the efficacy of mTOR inhibitors in cancer therapy [Rao R D, Buckner J C, Sarkaria J N.; Curr Cancer Drug Targets. 2004 December; 4(8):621-35. Mammalian target of rapamycin (mTOR) inhibitors as anti-cancer agents].

Rapamycin and rapamycin analogues have demonstrated activity against a broad range of human cancers growing in tissue culture and in human tumor xenograft models. The central role of mTOR in modulating cell proliferation in both tumour and normal cells and the importance of mTOR signalling for the hypoxic response suggest that rapamycin-based therapies may exert anti-tumour effects primarily through either inhibition of tumour cell proliferation or suppression of angiogenesis. Although rapamycin can induce apoptosis in select tumour models, rapamycin treatment typically slows growth but does not induce tumour regression, suggesting that tumour cell loss through apoptosis or other mechanisms are not major contributors to drug effect in most cases.

There have been many reports of drug delivery systems using hydrophobic polymers, such as poly(L-lactic acid), poly(lactic-co-glycolic acid), poly(caprolactone), polybutyl methacrylate, and poly(styrene-co-isobutylene-co-styrene). However, there are few reports of hydrogel microspheres loaded with paclitaxel. This is due to the poor compatibility between hydrophobic drugs and hydrogel microspheres [R. Shi, H. M. Burt, 'Amphiphilic dextran-graft-poly(epsilon-caprolactone) films for the controlled release of paclitaxel' International Journal of Pharmaceutics 271 (2004) 167, http://www.ptca.org/articles/taxus_profileframe.html D. S. Das, G. H. R. Rao, R. F. Wilson, T. Chandy, 'Controlled delivery of taxol from poly(ethylene glycol)-coated poly(lactic acid) microspheres' Journal of Biomedical Materials Research, 55 (2001) 96 R. T. Liggins, H. M. Burt, 'Paclitaxel loaded poly(L-lactic acid) microspheres: properties of microspheres made with low molecular weight polymers' International Journal of Pharmaceutics, 222 (2001) 19. J. K. Jackson, J. Smith, K. Letchford, K. A. Babiuk, L. Machan, P. Signore, W. L. Hunter, K. Wang, H. M. Burt, 'Characterisation of perivascular poly(lactic-co-glycolic acid) films containing paclitaxel' International Journal of Pharmaceutics, 283 (2004) 97. S. K. Dordunoo, J. K. Jackson, L. A. Arsenault, A. M. C. Oktaba, W. L. Hunter, H. M. Burt, 'Taxol encapsulation in poly(epsilon-caprolactone) microspheres' Cancer chemother. Parmacol. 36 (1995) 279.]

US2003/202936 discloses a process in which microspheres are prepared by immersing microparticles in a solution containing methanol and aminoacridine. Excess methanol is removed by evaporation, but this results in precipitation of the aminoacridine both inside and outside the microspheres.

Vandelli et al in the Journal of Controlled Release, 96(2004), 67-84 disclose microspheres in which diclofenac is precipitated in the core. The drug is uniformly distributed in each microparticle. The presence of drug on or close to the surface leads to rapid initial release of the drug, which is often undesirable.

According to the present invention there is provided a new process for forming drug-loaded polymer particles comprising the steps:

a) contacting particles comprising a matrix of water-insoluble polymer, which particles, when neat, are swellable in phosphate buffered saline (PBS) at room temperature to an equilibrium water content in the range of from 40% to 99% by weight based on polymer plus PBS, with a solution of a drug having a water solubility of less than 10 g/l at room temperature, in a first organic solvent; whereby a solution of drug in solvent becomes impregnated into the particles and the first solvent is selected to be capable of swelling neat particles;

b) separating drug solution which has not impregnated the particles in step a) from the impregnated particles;

c) contacting the impregnated particles with aqueous liquid whereby drug is precipitated in the core of the particles; and further comprising the steps d) and/or e)

d) rinsing the particles with drug precipitated within the core with a volatile, second solvent in which the particles are less swellable, relative to their swellability in water, and which is a solvent for the drug, wherein the drug solubility in the second solvent is at least 0.1 g/l, whereby drug on and close to the surface of the particles is removed with the second solvent;

e) drying the drug-loaded polymer particles by vacuum, or freeze drying, or air flow to remove the second solvent.

By "neat particles" we mean particles which are not impregnated with solvent, such as particles which have been dried by, for instance, lyophilisation or solvent drying.

When the solution of drug in a first solvent impregnates the particles, the solution mixes with any liquid which is already impregnated into the particles. The particles may either swell, or shrink. It is important that the drug remains in solution when the particles become impregnated with the drug solution.

Generally, the particles have a water content of less than 10% based on the weight of polymer matrix. This helps to ensure that the drug remains in solution, when the particles become impregnated.

Generally the particles are supplied at least partially swollen with aqueous impregnant liquor e.g. having at least 40% by weight water impregnated into the particles, based on the weight of polymer plus water. Since step a) requires the drug to remain in solution when the particles are impregnated, water-swollen particles must be subjected to preliminary steps to remove water. Although evaporation may be used to remove the water, it is more convenient to mix the particles, even in the presence of excess impregnant water, with a water-miscible solvent to swell the particles and replace absorbed water by solvent. The extracted water is removed from swollen particles as a liquid mixture with the solvent. Addition of further aliquots of the solvent is then made with removal of solvent/water mixtures, until the level of water is typically less than 10% based on the weight of polymer matrix. This procedure is referred to as prewashing hereinafter. The prewashing solvent is conveniently the same as the first solvent. The level of water remaining in the particles following the prewash, for instance when saturated with prewash solvent, calculated from the weight of solvent added to each step, the weight of water swollen into the matrix, the weight of mixed solvent and water removed in each step and the number of steps, assuming complete mixing and dilution of absorbed liquids as well as of non-absorbed liquids.

In the invention the first and second, volatile organic solvents are selected having regard to their ability to dissolve the drug and change the drug-loading capacity of the polymer particles. The first solvent is selected to be capable of swelling neat particles. The volatile solvent is mainly for the purpose of cleaning the polymer particle surface and preferably to extract water left in step c). The first and second (volatile) solvent may be the same as one another or may be different.

Preferably, the second (volatile) solvent has a boiling point of less than 90° C.

Preferably the first and/or second (volatile) solvents are those that swell the beads and can be water-miscible or water-immiscible. However in a less desirable form of the invention, solvents that shrink the beads can be used. Useful solvents include polar aprotic solvents such as dimethylsulphoxide (DMSO), a lactone, for example a pyrrolidone, such as 1-methyl-2-pyrrolidinone (NMP), dialkyl formamide, for instance dimethyl formamide (DMF), or a cyclic ether, for instance 1,4-dioxane ("dioxane"), but is preferably DMSO. The solvent may be a protic solvent, such as an alcohol.

The present invention has been found to be of utility for formulating drugs having anti-tumour properties and low solubility in water, with higher solubility in a water-miscible organic solvent. The invention is of particular utility for, for instance paclitaxel and derivatives having solubility in water at room temperature less than 10 g/l, rapamycin and derivatives having solubility in water at room temperature less than 10 g/l, dexamethasone and derivatives having solubility in water at room temperature less than 10 g/l, methotrexate, and some tecans with water-solubility less than 10 g/l. All of these compounds have a solubility ratio in a water-miscible solvent to water at room temperature of at least 10:1, preferably at least 100:1, up to as much as $10^6$:1 or even more, for instance more than $10^3$:1.

For these compounds the following table gives comparison water and solvent solubilities at room temperature. The ratio is of solubility in solvent:solubility in water (insoluble means less than 10 mg/l).

| Drug | Sol^y in water mg/l | Sol^y in DMSO | Sol^y Ratio |
|---|---|---|---|
| Paclitaxel | 0.3-30 | 50 | $>1.7 \times 10^3$ |
| Methotrexate | insol | 200 | $>5 \times 10^4$ |
| Rapamycin | 0.69 | 25 | $>4 \times 10^4$ |
| Dexamethasone | insol | 600 | $>10^5$ |
| Camptothecin | insol | 10 | $>10^3$ |

After prewashing, the polymer particles are impregnated with drug solution, and contact with the solution takes place for sufficient time for the particles to be loaded to equilibrium. Preferably, the particles are swollen to equilibrium. Alternatively the particles may be partially swollen, for instance to a solvent concentration of at least 50% equilibrium, more preferably at least 75% equilibrium concentration at room temperature. The degree of swelling may be monitored using a microscope. Swelling to equilibrium is reached when there is no further increase in average size (or volume) of the particle.

In the precipitation step (step c)), aqueous liquor is contacted with the solvent-laden particles for sufficient time to allow diffusion of water into the core of the particles and precipitation of drug to take place throughout the particles. Since the drug is water-insoluble, the use of excess aqueous liquor at this stage should lead to little by way of drug loss. Instead drug is immobilised by precipitating within the polymer matrix whereby it is immobilised.

Contact with aqueous liquor is generally carried out at a temperature <25° C. for a period of at least around 1 minute, preferably with agitation to optimise water/particle contact.

In the rinsing step, the solvent is contacted with the swollen particles for sufficient time to create a drug free layer on the particle surface. Selection of a suitable solvent for this step may involve a screening process in which water-swollen, but non-drug containing polymer particles are contacted with the solvent for varying periods of time, with the particles being observed before and after the solvent contact. Observation may be under a light microscope, optionally with measurement of the particle diameter and shape. Since the solvent could partially de-swell the polymer, particle size after the contact generally will be lower. The surfaces of the particles may also be observed to be less smooth, with angularities, or wrinkles.

The solvent for the rinsing step should also be selected such that the drug is at least slightly soluble in the solvent. The solubility should be at least 1 g/l. The rinsing step results in drug precipitate within a surface layer of the particles being dissolved and removed with rinsing solvent, to leave a relatively drug-free surface layer of polymer. This surface layer is dependent on the particle diameter and is generally around 1 to 100 μm thick, for instance about 30 μm thick. The thickness of the surface layer may be observed by placing the particles under an optical microscope. The polymer is substantially transparent, whereas the precipitated drug in the core of the particles renders this portion translucent or opaque. The particles therefore have a translucent or opaque core with a transparent halo of surface layer surrounding the core. The polymer, however, may be analysed and shown to comprise a chemically homogeneous material extending from the core to the outer surface of the particles, with the surface layer differing from the core material by the absence of drug.

According to the present invention there is also provided drug loaded polymer particles having a homogeneous polymer composition from the centre to the periphery, having precipitated drug in a core region thereof, which drug has a water solubility of less than 0.1 g/l at room temperature and having a surface layer in the range of from 1 to 100 μm thick, wherein the ratio of the concentration of drug in the core: concentration of drug in the surface layer is at least 2:1, preferably at least 10:1, more preferably at least 100:1.

Preferably, the drug has a solubility in a solvent selected from dimethyl sulfoxide (DMSO), 1-methyl-2-pyrrolidinone (NMP), dimethyl formamide (DMF) and dioxane to a concentration of at least $10^1$, preferably at least $10^2$, times the solubility in water at room temperature.

The polymer which is used to form the particles should be a relatively hydrophilic polymer that must be water-insoluble. By water-insoluble we mean that the polymer will not dissolve in water, or may be swollen by water, but constrained from total dissolution by physical or chemical crosslinks. The polymer thus forms the hydrogel on contact with water. A hydrogel may comprise, for instance, at least 40%, preferably at least 60%, more preferably at least 75%, preferably more than 80%, more preferably more than 90% and most preferably at least 95% water when the particles are swollen to equilibrium in PBS at room temperature. The equilibrium water content after swelling to equilibrium may be tested by gravimetric methods.

The beads before loading with drug have a diameter substantially all in the range 25 to 1500 μm, preferably in the range 50 to 1200 μm, for instance in the range 100 to 1200 μm measured in PBS at room temperature by optical microscopy.

In the invention the term bead is intended to cover particles of all shapes, for instance rod shapes, cubes, irregular and non-uniform shapes. However the invention is of most benefit where the beads are spherical, spheroidal or pellet shaped, or disk shaped. In non-spherical particles, such as pellets, spheroids or disks, the maximum dimension is preferably no more than three times the minimum diameter, and preferably less than two times the minimum diameter, for instance around 1.5 or less. The size limitations mentioned above are determined by testing a sample of the swellable beads under conditions in which the beads are swollen to equilibrium in phosphate buffered saline at room temperature and the sizes are measured using an optical microscope.

The compositions are preferably provided with a particle size specification which defines the spread of diameters. Preferably the beads are graded into calibrated size ranges for accurate embolisation of vessels. The particles preferably have sizes when equilibrated in PBS at room temperature, in the range 100 to 1500 μm, more preferably in the range 100 to 1200 μm. The calibrated ranges may comprise beads having diameters with a nominal bandwidth of about 100 to 300 μm. The nominal size ranges may be for instance 100 to 300 μm, 300 to 500 μm, 500 to 700 μm, 700 to 900 μm and 900 to 1200 μm.

Preferably the polymer comprises alcoholic hydroxyl groups or acylated derivatives thereof. In one embodiment polymers are used which are derived from natural sources, such as albumin, alginate, gelatin, starch, chitosan or collagen, all of which have been used as embolic agents. In a preferred embodiment the polymer is substantially free of naturally occurring polymer or derivatives. It is preferably formed by polymerising ethylenically unsaturated monomers including monomers having hydroxyalkyl or acyloxyalkyl groups in the presence of di- or higher-functional crosslinking monomers. The ethylenically unsaturated monomers may include an ionic (including zwitterionic) monomer.

Copolymers of hydroxyethyl methacrylate, acrylic acid and cross-linking monomer, such as ethylene glycol dimethacrylate or methylene bisacrylamide, as used for etafilcon A based contact lenses may be used. Copolymers of N-acryloyl-2-amino-2-hydroxymethyl-propane-1,3-diol and N,N-bisacrylamide may also be used.

Other polymers are cross-linking styrenic polymers e.g. with ionic substituents, of the type used as separation media or as ion exchange media.

Another type of polymer which may be used to form the water-swellable water-insoluble matrix is polyvinyl alcohol crosslinked using aldehyde-type crosslinking agents such as glutaraldehyde. For such products, the polyvinyl alcohol (PVA) may be rendered ionic by providing pendant ionic groups by reacting a functional ionic group containing compound with the hydroxyl groups. Examples of suitable functional groups for reaction with the hydroxyl groups are acylating agents, such as carboxylic acids or derivatives thereof, or other acidic groups which may form esters.

The invention is of particular value where the polymer matrix is formed from a polyvinyl alcohol macromer, having more than one ethylenically unsaturated pendant group per molecule, by radical polymerisation of the ethylenic groups. Preferably the PVA macromer is copolymerised with ethylenically unsaturated monomers for instance including a nonionic and/or ionic monomer including anionic monomer.

The PVA macromer may be formed, for instance, by providing PVA polymer, of a suitable molecular weight such as in the range 1000 to 500,000 D, preferably 10,000 to 100,000 D, with pendant vinylic or acrylic groups. Pendant acrylic groups may be provided, for instance, by reacting acrylic or methacrylic acid with PVA to form ester linkages through some of the hydroxyl groups. Other methods for attaching vinylic groups capable of polymerisation onto polyvinyl alcohol are described in, for instance, U.S. Pat. No. 4,978,713 and, preferably, U.S. Pat. Nos. 5,508,317 and 5,583,163. Thus the preferred macromer comprises a backbone of polyvinyl alcohol to which is linked, via a cyclic acetal linkage, an (alk)acrylaminoalkyl moiety. Example 1 describes the synthesis of an example of such a macromer known by the approved named nelfilcon B. Preferably the PVA macromers have about 2 to 20 pendant ethylenic groups per molecule, for instance 5 to 10.

Where PVA macromers are copolymerised with ethylenically unsaturated monomers including an ionic monomer, the ionic monomer preferably has the general formula I $$Y^1BQ^1 \qquad I$$

in which $Y^1$ is selected from

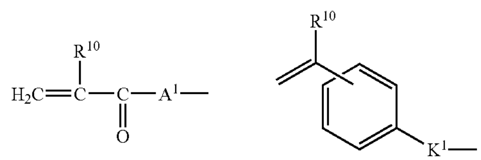

$CH_2{=}C(R^{10})—CH_2—O—$, $CH_2{=}C(R^{10})—CH_2OC(O)—$, $CH_2{=}C(R^{10})OC(O)—$, $CH_2{=}C(R^{10})—O—$, $CH_2{=}C(R^{10})CH_2OC(O)N(R^{11})—$, $R^{12}OOCCR^{10}{=}CR^{10}C(O)—O—$, $R^{10}CH{=}CHC(O)O—$, $R^{10}CH{=}C(COOR^{12})CH_2—C(O)—O—$,

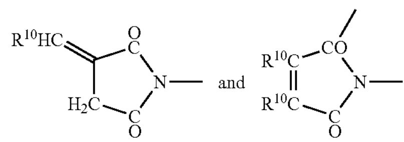

wherein:

$R^{10}$ is hydrogen or a $C_1$-$C_4$ alkyl group;

$R^{11}$ is hydrogen or a $C_1$-$C_4$ alkyl group;

$R^{12}$ is hydrogen or a $C_1$-$C_4$ alkyl group or $BQ^1$ where B and $Q^1$ are as defined below;

$A^1$ is —O— or $—NR^{11}—$;

$K^1$ is a group $—(CH_2)_rOC(O)—$, $—(CH_2)_rC(O)O—$, $—(CH_2)_rOC(O)O—$, $—(CH_2)_rNR^{13}—$, $—(CH_2)_rNR^{13}C(O)—$, $—(CH_2)_rC(O)NR^{13}—$, $—(CH_2)_rNR^{13}C(O)O—$, $—(CH_2)_rOC(O)NR^{13}—$, $—(CH_2)_rNR^{13}C(O)NR^{13}—$ (in which the groups $R^{13}$ are the same or different), $—(CH_2)_rO—$, $—(CH_2)_rSO_3—$, or, optionally in combination with B, a valence bond and r is from 1 to 12 and $R^{13}$ is hydrogen or a $C_1$-$C_4$ alkyl group;

B is a straight or branched alkanediyl, oxaalkylene, alkanediyloxaalkanediyl, or alkanediyloligo(oxaalkanediyl) chain optionally containing one or more fluorine atoms up to and including perfluorinated chains or, if $Q^1$ or $Y^1$ contains a terminal carbon atom bonded to B a valence bond; and $Q^1$ is an ionic group.

Such a compound including an anionic group $Q^1$ is preferably included.

An anionic group $Q^1$ may be, for instance, a carboxylate, carbonate, sulphonate, sulphate, nitrate, phosphonate or phosphate group. The monomer may be polymerised as the free acid or in salt form. Preferably the $pK_a$ of the conjugate acid is less than 5.

A suitable cationic group $Q^1$ is preferably a group $N^+R^{14}{}_3$, $P^+R^{15}{}_3$ or $S^+R^{15}{}_2$ in which the groups $R^{14}$ are the same or different and are each hydrogen, $C_{1-4}$-alkyl or aryl (preferably phenyl) or two of the groups $R^{14}$ together with the heteroatom to which they are attached from a saturated or unsaturated heterocyclic ring containing from 5 to 7 atoms the groups $R^{15}$ are each $OR^{14}$ or $R^{14}$. Preferably the cationic group is permanently cationic, that is each $R^{14}$ is other than hydrogen. Preferably a cationic group Q is $N^+R^{14}{}_3$ in which each $R^{14}$ is $C_{1-4}$-alkyl, preferably methyl.

A zwitterionic group $Q^1$ may have an overall charge, for instance by having a divalent centre of anionic charge and monovalent centre of cationic charge or vice-versa or by having two centres of cationic charge and one centre of anionic charge or vice-versa. Preferably, however, the zwitterion has no overall charge and most preferably has a centre of monovalent cationic charge and a centre of monovalent anionic charge.

Examples of zwitterionic groups which may be used as Q in the present invention are disclosed in WO-A-0029481.

Where the ethylenically unsaturated monomer includes zwitterionic monomer, for instance, this may increase the hydrophilicity, lubricity, biocompatibility and/or haemocompatibility of the particles. Suitable zwitterionic monomers are described in our earlier publications WO-A-9207885, WO-A-9416748, WO-A-9416749 and WO-A-9520407. Preferably a zwitterionic monomer is 2-methacryloyloxy-2'-trimethylammonium ethyl phosphate inner salt (MPC).

In the monomer of general formula I preferably $Y^1$ is a group $CH^2{=}CR^{10}COA$- in which $R^{10}$ is H or methyl, preferably methyl, and in which $A^1$ is preferably NH. B is preferably an alkanediyl group of 1 to 12, preferably 2 to 6 carbon atoms. Such monomers are acrylic monomers.

There may be included in the ethylenically unsaturated monomer diluent monomer, for instance non-ionic monomer. Such a monomer may be useful to control the $pK_a$ of the acid groups, to control the hydrophilicity or hydrophobicity of the product, to provide hydrophobic regions in the polymer, or merely to act as inert diluent. Examples of non-ionic diluent monomer are, for instance, alkyl(alk) acrylates and (alk) acrylamides, especially such compounds having alkyl groups with 1 to 12 carbon atoms, hydroxy, and di-hydroxy-substituted alkyl(alk) acrylates and -(alk) acrylamides, vinyl lactams, styrene and other aromatic monomers.

In the polymer matrix, the level of anion is preferably in the range 0.1 to 10 meq $g^{-1}$, preferably at least 1.0 meq $g^{-1}$. Preferred anions are derived from strong acids, such as sulphates, sulphonates, phosphates and phosphonates.

Where PVA macromer is copolymerised with other ethylenically unsaturated monomers, the weight ratio of PVA macromer to other monomer is preferably in the range of 50:1 to 1:5, more preferably in the range 20:1 to 1:2. In the ethylenically unsaturated monomer the anionic monomer is preferably present in an amount in the range 10 to 100 mole %, preferably at least 25 mole %.

The crosslinked polymer may be formed as such in particulate form, for instance by polymerising in droplets of monomer in a dispersed phase in a continuous immiscible carrier. Examples of suitable water-in-oil polymerisations to produce particles having the desired size, when swollen, are known. For instance U.S. Pat. No. 4,224,427 describes processes for forming uniform spherical beads (microspheres) of up to 5 mm in diameter, by dispersing water-soluble monomers into a continuous solvent phase, in a presence of suspending agents. Stabilisers and surfactants may be present to provide control over the size of the dispersed phase particles. After polymerisation, the crosslinked microspheres are recovered by known means, and washed and optionally sterilised. Preferably the particles, e.g. microspheres, are swollen in an aqueous liquid, and classified according to their size.

In the invention the steps in which the particles are contacted with liquid are generally conducted in the presence of excess liquid, for instance in a vessel with agitation. Alternative methods to contacting the particles with the liquid are:

immersion without agitation, immersion with sonication, continuous flow and fluidised bed. Liquid and loaded particles are generally separated from one another, for instance by one or a combination of the following methods: pipetting, decantation, filtration, evaporation, liquid exchange, aspiration or lyophilisation. If required, the particles may, at the end of the process, be dried, for instance by lyophilisation or solvent drying and may then be sterilised by autoclaving or gamma irradiation.

The following is a brief description of the figures:

FIG. 3A shows dried beads with 7.2 mg paclitaxel loading, 3B shows rehydrated beads of 3A, 3C shows dried beads with 23.9 mg/ml paclitaxel loading and 3D shows rehydrated beads of 3C;

Figure 8:
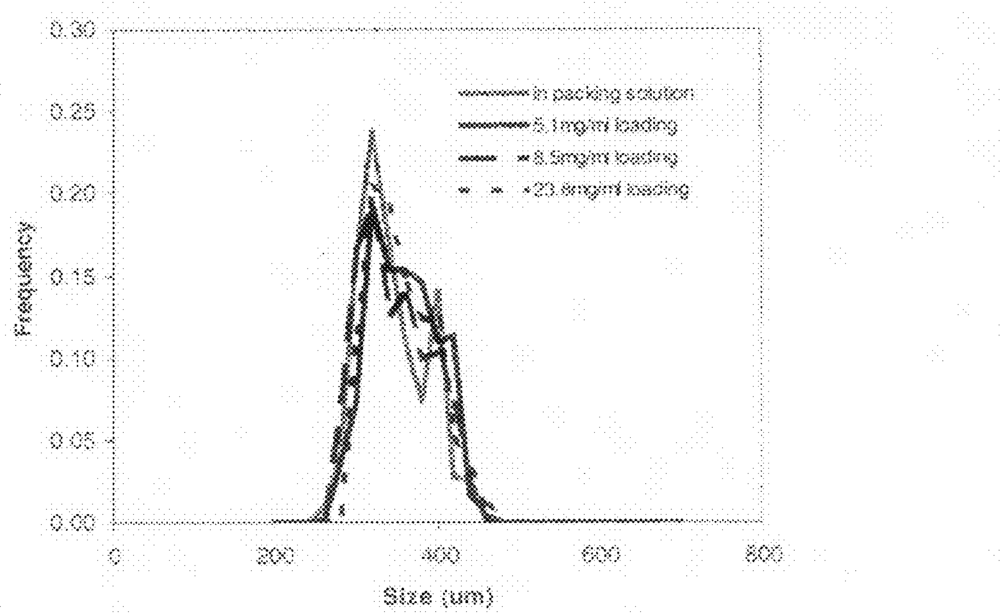
Figure 9:
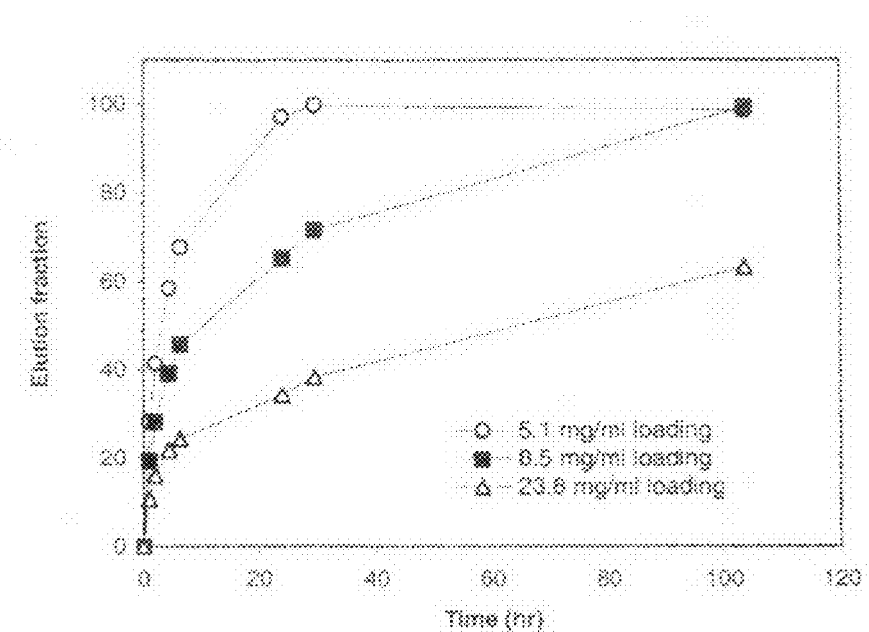
Figure 10:
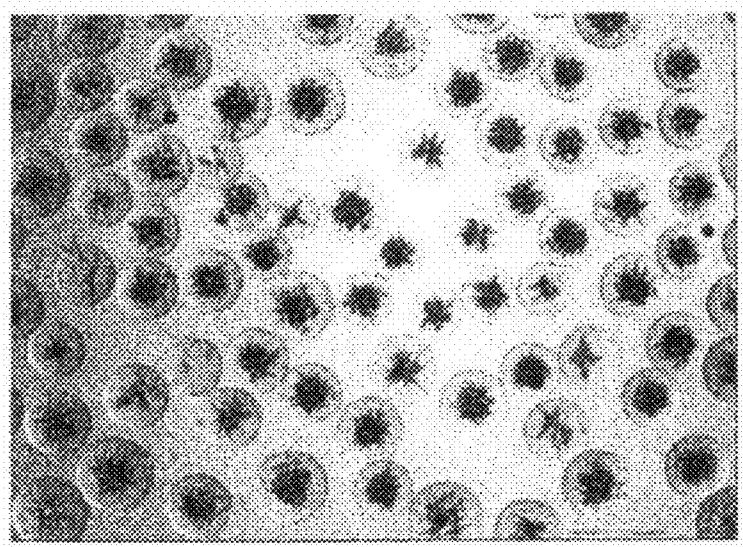

FIGS. 7A to D are photographs showing rapamycin loaded beads using the method of Example 2. FIG. 7A shows 300 to 500 μm unloaded bead, FIG. 7B shows 300 to 500 μm samples of the bead loaded with 5.1 mg/ml rapamycin, FIG. 7C shows the 300 to 500 μm beads loaded with 8.5 mg/ml rapamycin and FIG. 7D shows the beads loaded with 23.8 mg/ml rapamycin, all as described in Example 2;

FIG. 8 shows the size distribution of rapamycin beads as produced in Example 2;

FIG. 9 shows the elution profile of the beads with the three loading levels in Example 2;

FIG. 10 shows certain micrographs of dexamethasone loaded beads as described in Example 3.

The invention is illustrated in the following Examples:

EXAMPLE 1

Preparation of paclitaxel loaded microspheres is as described in WO2004/000548 Example 1, "high AMPS" product. Briefly, an aqueous mixture of polyvinyl alcohol macromer having acetal-linked ethylenically unsaturated groups and 2-acrylamido-2-methyl-propane sulphonate in a weight ratio of about 1:1 is suspended in a continuous phase of butyl acetate containing cellulose acetate butyrate stabiliser with agitator and is radically polymerised using redox initiation to form beads, which are washed, dyed and sieved into size fractions including the 300-500 μm, 500-700 μm and 700-900 μm fractions used in subsequent Examples. The equilibrium water content of the microspheres is 94 to 95% by weight.

Figure 1:
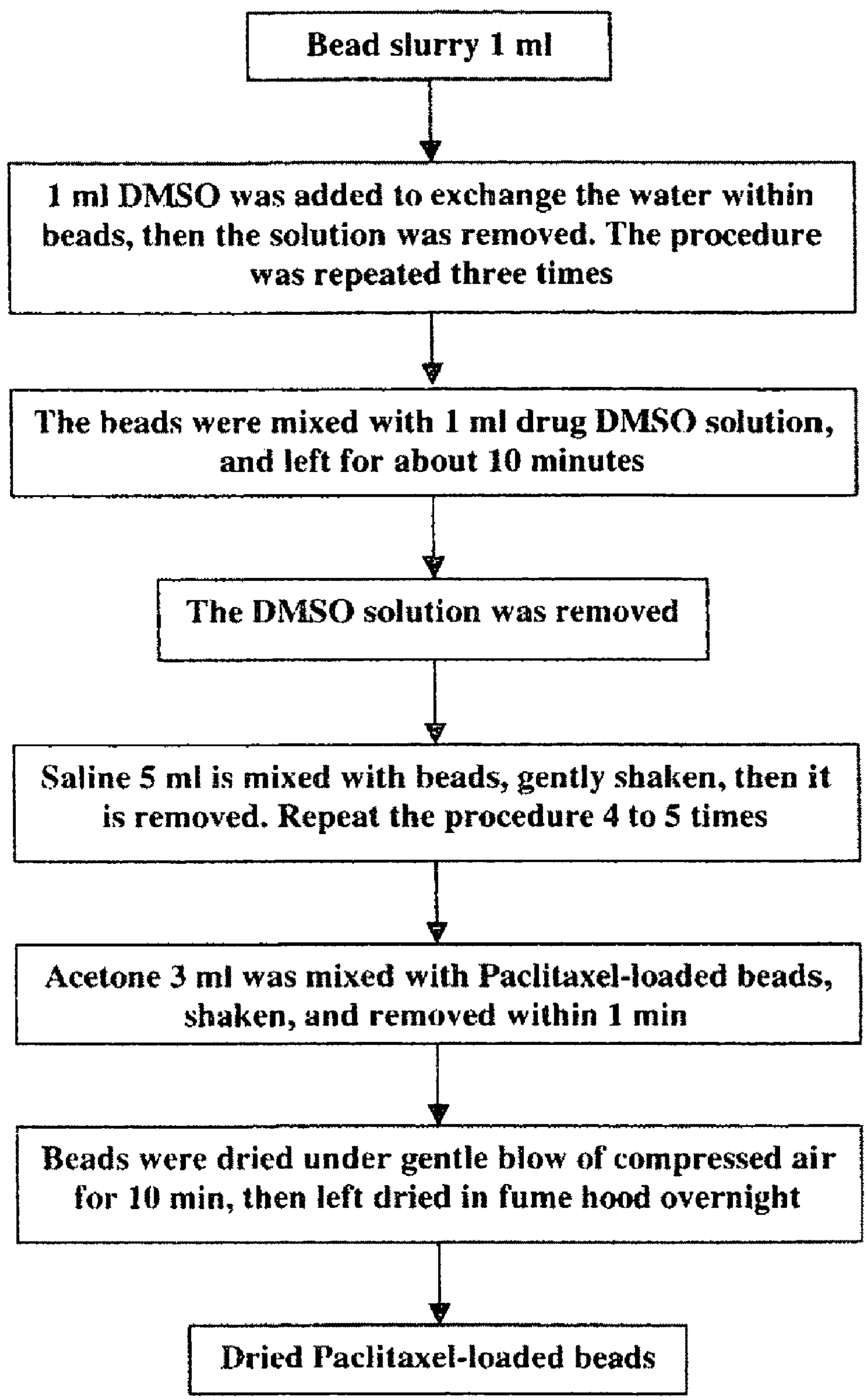
FIG. 1 is a flow chart showing the process steps for Example 1 and others.

The loading procedure is shown schematically in FIG. 1. First, the aqueous packing solution of 1 ml beads was removed from the vial, and the beads were fully mixed with 1 ml DMSO by gently shaking. After 5 minutes the DMSO/water mixture was removed and 1 ml fresh DMSO was added again. The procedure was carried out three times, and a bead slurry was finally obtained by removing DMSO which also contained some removed water. The water content at this stage is less than 10% based on the swollen weight assuming that DMSO equilibrates into the swollen beads and based on the total volumes of water initially present as swollen into the beads and DMSO added, taking into account the volume of mixed solvents removed after each wash step.

16.4 mg paclitaxel (Taxol®) powder was dissolved in 1 ml DMSO in a vial. Subsequently, the prewashed water-depleted microsphere slurry was mixed with the solution, and gently shaken for 10 minutes to enable the drug to completely diffuse into the beads. After this the DMSO solution was removed, 5 ml saline was added to the beads and the mixture was agitated. Paclitaxel precipitates were observed in solution, and the blue beads became a white colour due to the precipitation of paclitaxel within the rehydrated beads as solvent changed. After removing the solution and paclitaxel precipitates, 5 ml of fresh saline was added, and the procedure was repeated 5 times to remove paclitaxel crystals in solution and the residual DMSO.

The surface of the paclitaxel-loaded beads had attached to it many small drug crystals, and the paclitaxel domain inside the beads was not physically stable (tending to recrystallise outside the beads). In addition paclitaxel has been reported as not chemically stable in aqueous solution. Therefore, the paclitaxel-loaded beads need to be dried.

The paclitaxel-loaded bead slurry was washed with 3 ml acetone for about 1 minute, and the acetone was removed quickly by aspiration. Then the beads were dried under a gentle stream of compressed air in an isolator for about 10 minutes. The beads were further dried by being left in a fume hood overnight.

Figure 2:
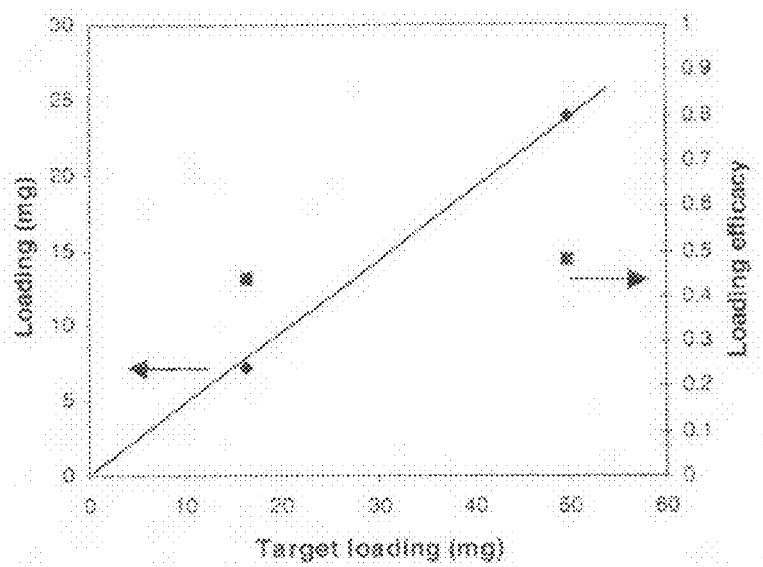
FIG. 2 shows the loading efficacy of paclitaxel against target loading for Example 1.

The paclitaxel loading was analysed by HPLC method. 4.1 mg of paclitaxel-loaded beads were extracted with 1 ml DMSO under ultrasonication for 2 hr, subsequently extracted with fresh DMSO 1 ml 5 times. The collected DMSO was analysed by Waters 486 HPLC system using a Phenomenex Luna C18 column (column temperature: 40° C.); mobile phase: methanol 63, ammonium acetate buffer (pH 3) 33, isopropanol 4 mixture; UV detector at 230 nm. The paclitaxel loading efficacy against target loading (i.e. initial total amount of drug in solution) is shown in FIG. 2.

The rehydration capability of the loaded beads was assessed by optical microscopy comparing the size of the loaded beads before and after rehydration. The volume increase of the rehydrated beads is contributed from the water uptake during bead swelling. In this case the drug elution amount was neglected. The dried beads with 7.2 mg/ml paclitaxel loading had an average diameter of 353±25 μm. After rehydration for 12 h, the swollen beads had an average diameter of 810±46 μm. For the high loading beads with 23.9 mg/ml paclitaxel, the average diameter of dry beads is 399±20 μm. The average diameter after 12 h rehydration is 832±45 μm.

Figure 3:
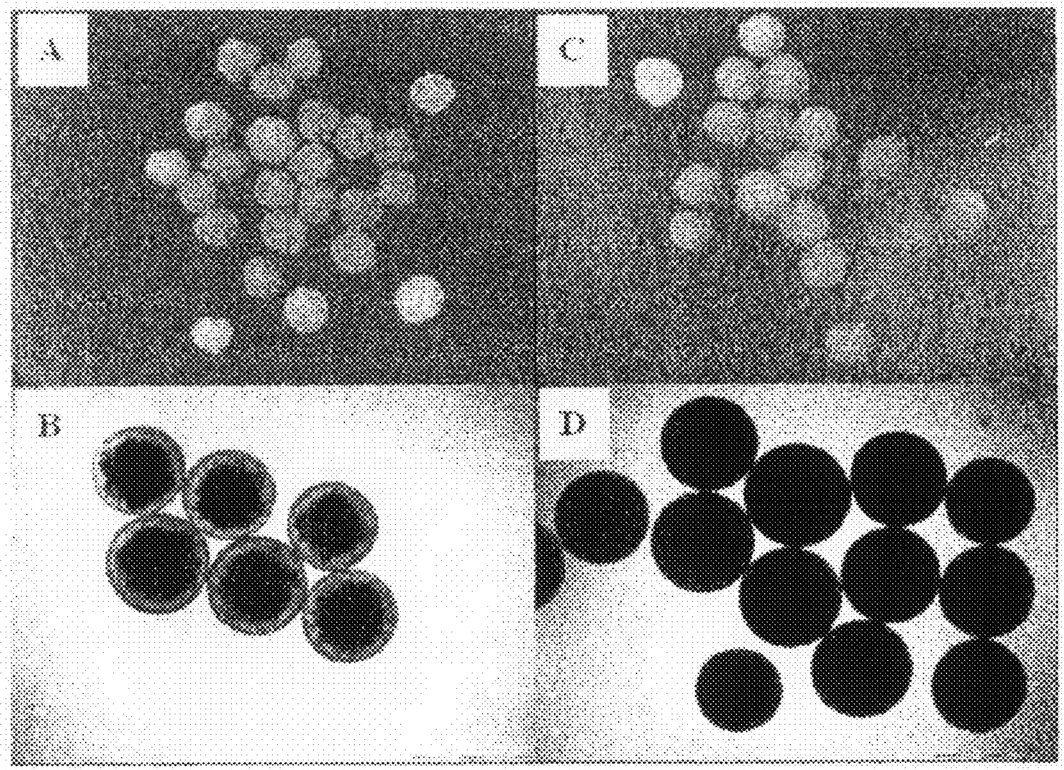
FIG. 3 shows microscopy pictures of dried beads and rehydrated beads as described in Example 1.

FIG. 3 shows photos taken by using an Olympus microscope with a ColorView camera. FIGS. 3A and 3C are the photographs of dried paclitaxel-loaded beads, which show an irregular surface morphology. After rehydration, the beads swell back to spherical shape (FIGS. 3B and 3D).

Figure 4:
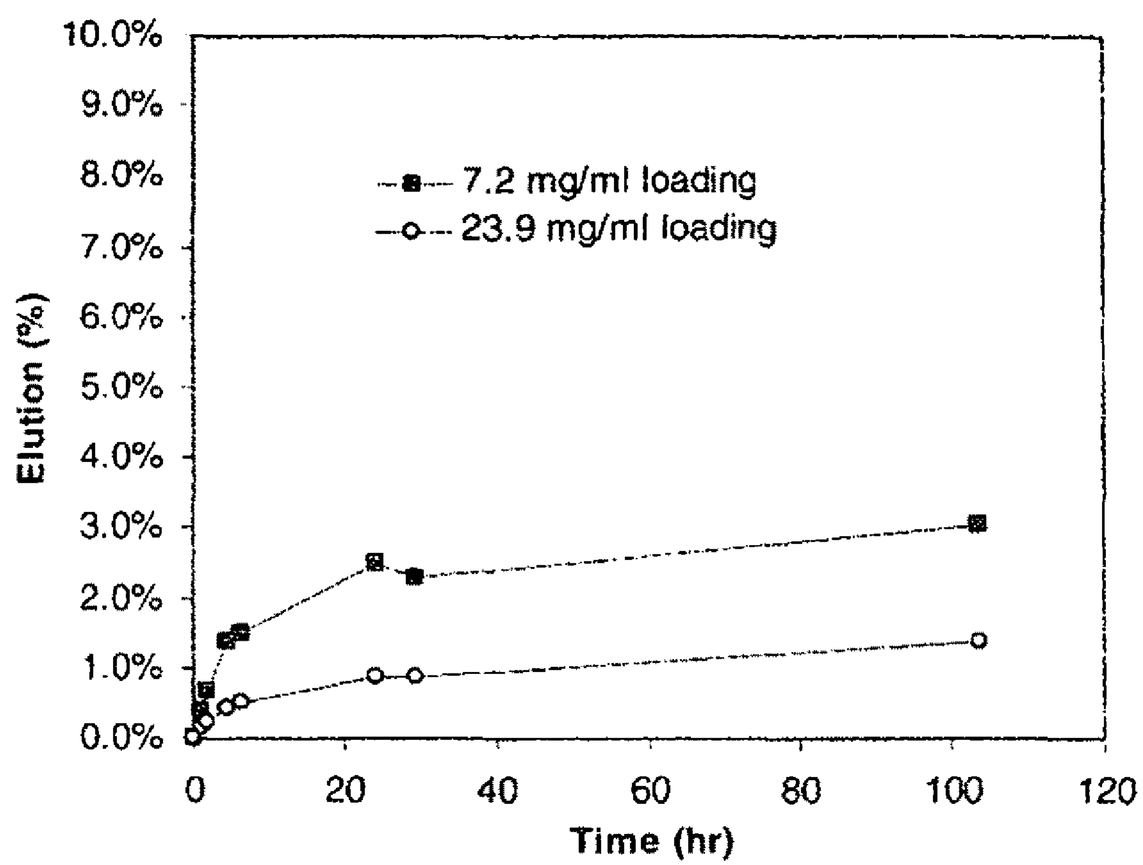
FIG. 4 shows the elution profile for paclitaxel from product formed in Example 1.

15.8 mg of dried paclitaxel-loaded beads were mixed with 200 ml PBS buffer on a roller mixer under room temperature. Two test samples were used, one loaded with 7.2 mg/ml paclitaxel and the other with 23.9 mg/ml paclitaxel. At predetermined time interval, 100 ml solution was removed and fresh PBS was added. The elution was determined HPLC processing as for FIG. 2. The profile is shown in FIG. 4.

EXAMPLE 2

Preparation of Rapamycin-Loaded Microspheres

Figure 5:
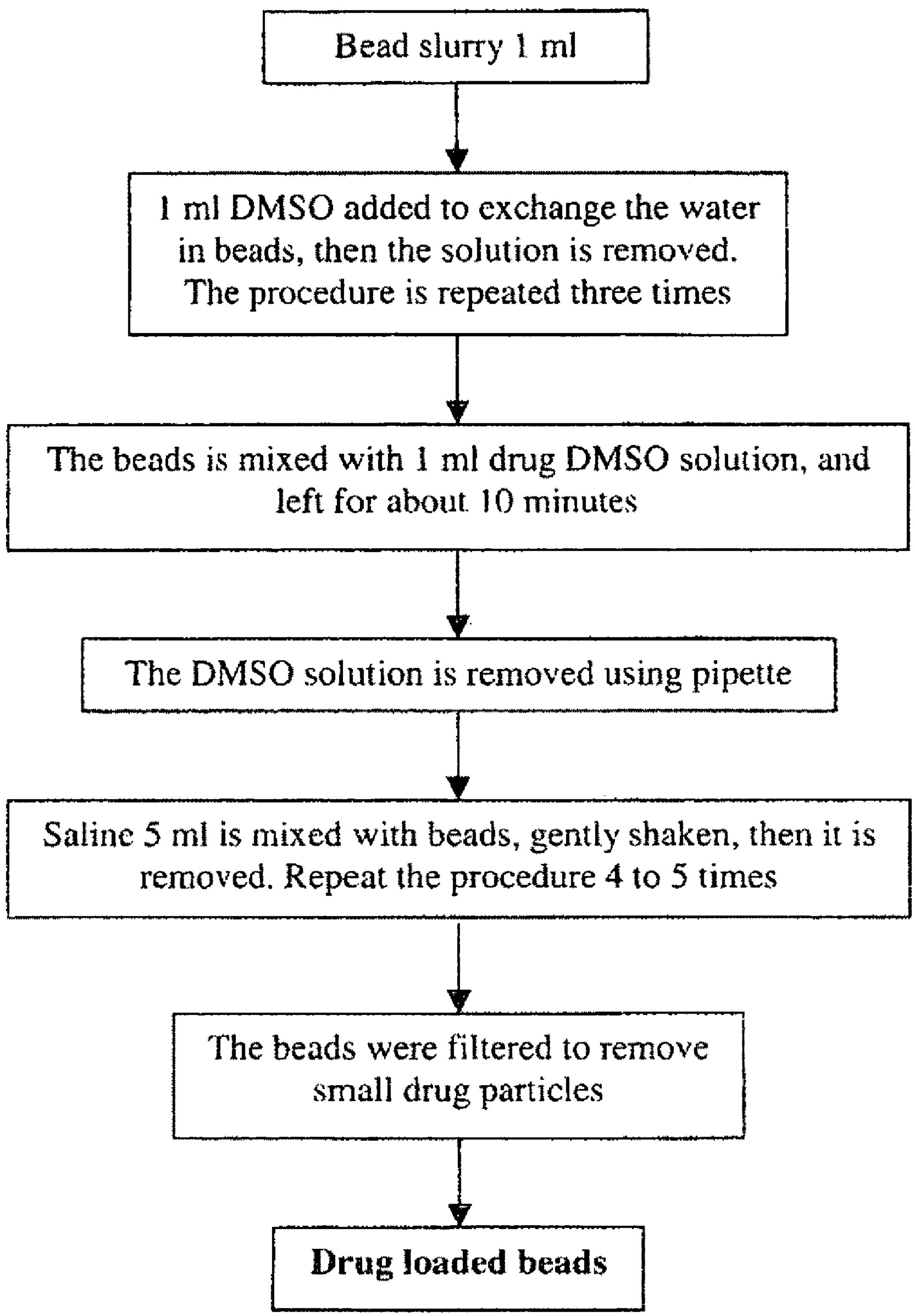
FIG. 5 shows a flow chart for the preparation process used in Example 2.

In this Example the microspheres were 300-500 μm PVA beads (as used in Example 1). The loading procedure is shown in FIG. 5. First, the aqueous packing solution of 1 ml beads was removed, and the beads were fully mixed with 1 ml DMSO by gently shaking. After 5 minutes the DMSO was removed and 1 ml fresh DMSO was added again. The procedure was repeated three times, and a bead slurry was finally obtained by removing DMSO.

Rapamycin powder (16.4 mg) was dissolved in 1 ml DMSO in a vial. Subsequently, the pre-washed water-depleted microspheres were mixed with the rapamycin solution, and gently shaken for 10 minutes to enable the drug to completely diffuse into the beads. After this the DMSO solution was removed, 5 ml of saline was added to the beads and the mixture was agitated. Rapamycin precipitates were observed in solution, and the blue beads became white in colour due to the solubility decrease of rapamycin within the rehydrated beads. After removing the solution and rapamycin precipitates, 5 ml of fresh saline was added, and the procedure was repeated 5 times to remove rapamycin solid in solution and the residual DMSO.

Figure 6:
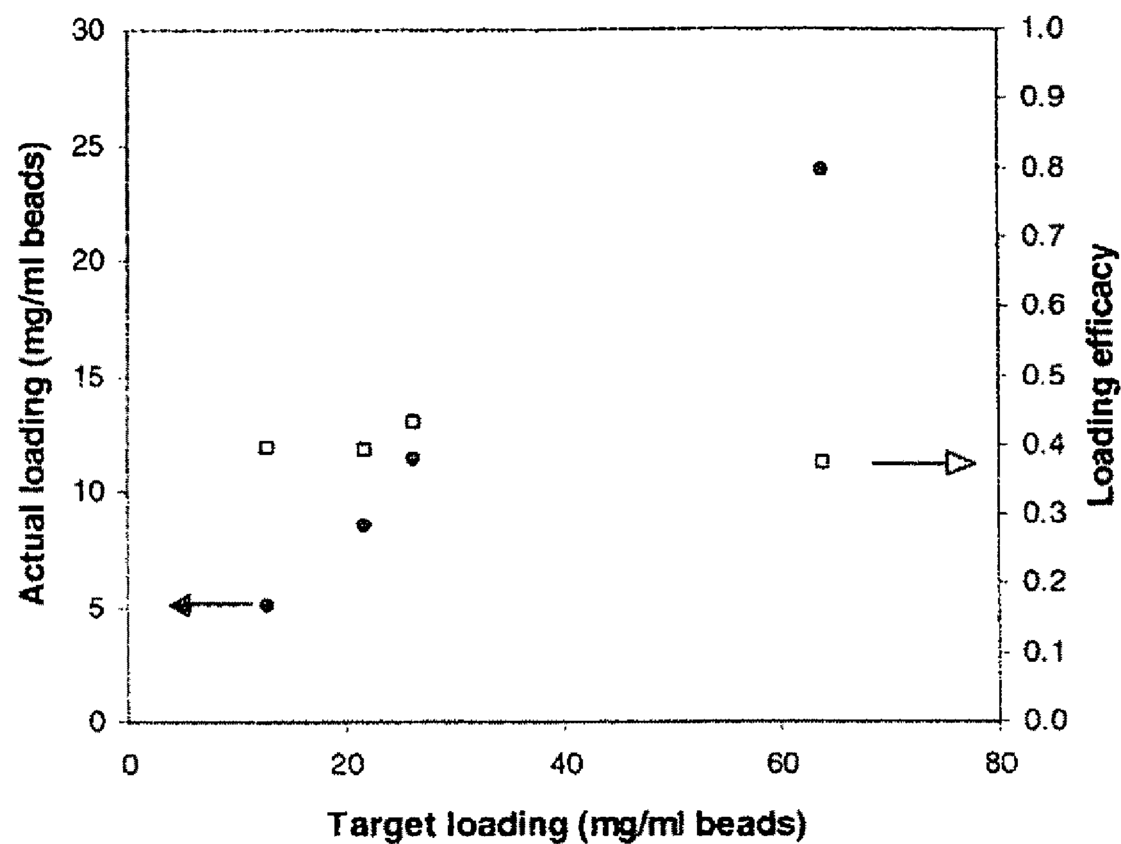
FIG. 6 shows rapamycin loading efficacy in PVA beads using the method described in Example 2.

The rapamycin loading was analysed by UV at 280 nm. 0.5 ml of rapamycin-loaded beads was extracted with 2 ml DMSO 6 times. The actual loading and loading efficacy against target drug loading were show in FIG. 6. The UV analysis indicates that rapamycin loading efficacy is 40±3% at different target loading.

Figure 7:
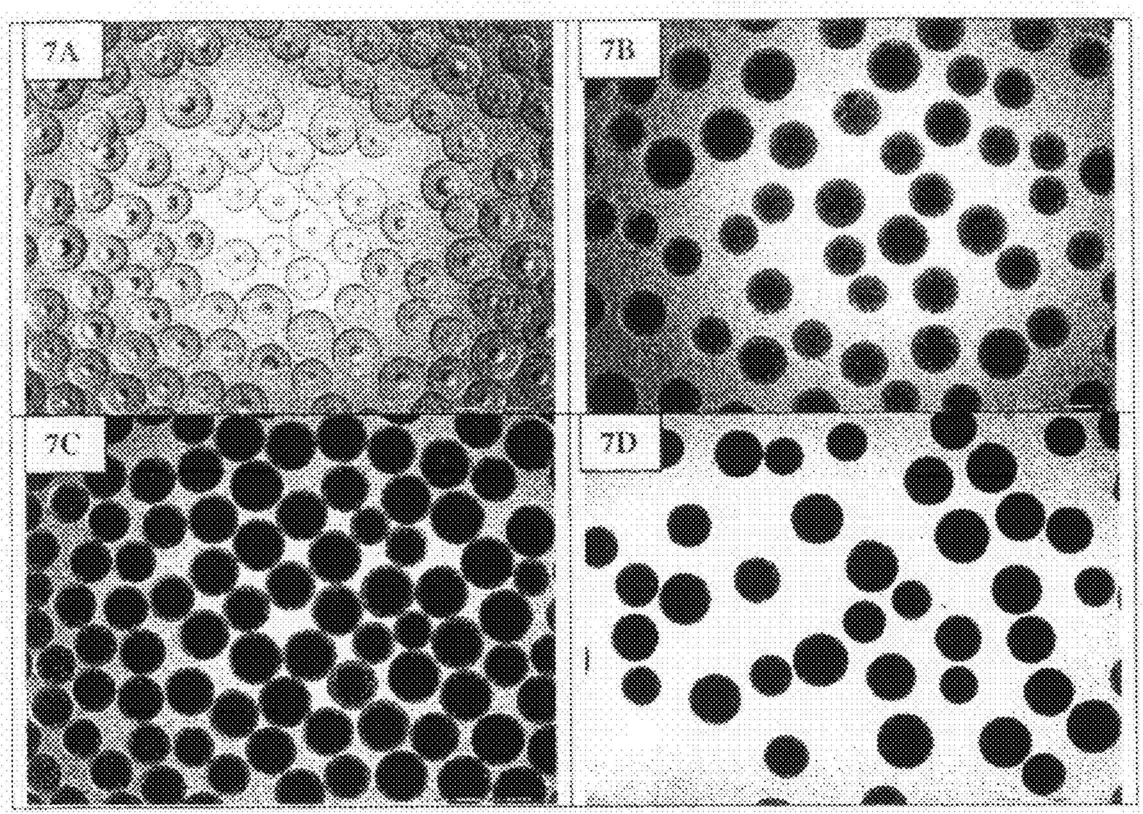

FIG. 7 shows the photos taken by using an Olympus microscope with a ColorView camera. FIG. 7A is the photograph of beads before rapamycin loading, which shows the transparent microspheres. After loading, the beads were no longer transparent (FIG. 7B, 7C, 7D), but still kept their spherical shape. FIG. 8 shows the histogram of size distribution of beads with/without rapamycin loading in saline. It demonstrates that rapamycin loading has little effect on bead size distribution.

0.5 ml of rapamycin-bead slurry with different loading was mixed with 200 ml PBS buffer on a roller mixer under room temperature. At predetermined time intervals, 100 ml solution was removed and fresh PBS was added. The concentration of rapamycin in the PBS is determined by UV at 280 nm. The elution profile was shown in FIG. 9.

EXAMPLE 3

Preparation of Dexamethasone-Loaded Microspheres

Following the procedure in Example 2 and FIG. 5, dexamethasone was loaded into PVA beads (300-500 μm) as used in Example 1. First, the aqueous packing solution of 1 ml beads was removed, and the beads were fully mixed with 1 ml DMSO by gently shaking. After 5 minutes the DMSO was removed and 1 ml fresh DMSO was added again. The procedure was repeated three times, and a bead slurry was finally obtained by removing DMSO.

Dexamethasone powder (139.6 mg) was dissolved in 1 ml DMSO in a vial. The solubility of dexamethasone in DMSO at room temp is about 60 g/l, and it is practically insoluble in water. Subsequently, the pre-washed water-depleted microspheres were mixed with the dexamethasone solution, and gently shaken for 10 minutes to enable the drug to completely diffuse into the beads. After this the DMSO solution was removed, 5 ml saline was added to the beads and the mixture was agitated. Dexamethasone precipitates were observed in solution, and the blue beads became white colour due to the solubility decrease precipitation of dexamethasone within the rehydrated beads as solvent changed. After removing the solution and suspended dexamethasone precipitates, 5 ml of fresh saline was added, and the procedure was repeated 5 times to clear dexamethasone solid in solution and the residual DMSO. Photographs of the dexamethasone-loaded beads under an optical microscope are shown in FIG. 10. There is a thin surface layer with substantially no drug. It is believed that the surface layer of drug is removed at the first step in which aqueous liquid is added (saline to precipitate the drug) since at this stage there is sufficient solvent present in the liquid mixture to keep the drug in solution at the surface so that it is removed with the saline and further saline rinses.

EXAMPLE 4

Paclitaxel Loading by Different Solvent

Other water-miscible solvents, including 1-methyl-2-pyrrolidinone, N,N-dimethylformamide, and 1,4-dioxane were utilised in place of DMSO to load paclitaxel into beads (as used in Example 1). The procedures were otherwise the same as that described in Example 1. Beads (500-700 μm) were used in this experiment. Before paclitaxel loading, the beads were washed with the selected organic solvent and saturated while depleting the water content values of below 15%. For each solvent adequate dilution is achieved with three washing steps. It was found that 1-methyl-2-pyrrolidinone made the beads swell; N,N-dimethylformamide and dioxane decreased the bead sizes the size when swollen to equilibrium in PBS at room temperature. 1 ml of the organic solvent with dissolved paclitaxel powder of the concentration shown in the table below was mixed with the beads above and left for 15 to 30 minutes. After saline precipitation then washing and acetone rinsing, the beads were dried under a gentle stream of compressed air, then in fume hood. The loaded paclitaxel was extracted with DMSO and analysed by HPLC. The results were listed in the Table below.

Paclitaxel solution concentrations and loading efficiency in beads with organic solvents

| Solvent | Solution Concⁿ g/l | Loading efficiency |
| --- | --- | --- |
| 1-methyl-2-pyrrolidinone | 28.4 | 10.1% |
| N,N-dimethylformamide | 43.9 | 6.4% |
| 1,4-dioxane | 31.1 | 0.8% |

The invention claimed is:

1. A process for forming drug-loaded polymer particles comprising the steps:

a) providing particles comprising a matrix of water-insoluble polymer, which, when neat, are swellable in phosphate buffered saline (PBS) at room temperature to an equilibrium water content in the range of from 40% to 99% by weight based on polymer plus PBS;

b) providing a solution of a drug having a water solubility of less than 10 g/l at room temperature, in a first organic solvent is selected to be capable of swelling neat particles;

c) containing the particles with the solution of drug whereby a solution of drug in solvent becomes impregnated into the particles;

d) separating drug solution which has not impregnated the particles in step c) from the impregnated particles and recovering the impregnated particles;

e) contacting the impregnated particles with aqueous liquid whereby drug is precipitated in the core of the particles;

f) providing a volatile, second solvent in which the particles are less swellable, relative to their swellability in water, and which is a solvent for the drug, wherein the drug solubility in the second solvent is at least 0.1 g/l; and g) rinsing the particles produced in step e) with the second solvent whereby drug on and close to the surface of the particles is removed with the second solvent; and, optionally h) drying the drug-loaded polymer particles by vacuum, or freeze drying, or air flow to remove the second solvent.

2. A process according to claim 1, wherein the particles swell in step c) when the solution of drug becomes impregnated into the particles.

3. A process according to claim 2, wherein the particles are swollen to equilibrium when the solution of drug becomes impregnated into the particles.

4. A process according to claim 1, in which the first and second solvents are the same.

5. A process according to claim 1, in which the first and second solvents are different to one another.

6. A process according to claim 1, in which the first and/or second solvent is miscible with water.

7. A process according to claim 1, wherein the second solvent has a boiling point of less than 90° C.

8. A process according to claim 1, in which the ratio of drug solubilities at room temperature in the first organic solvent and water is in the range 10:1 to $10^6$:1.

9. A process according to claim 1, in which the drug is selected from the group consisting of rapamycin analogues, esters and salts thereof which have water solubility less than 0.1 g/l; paclitaxel; analogues, esters and salts thereof which have water solubility less than 0.1 g/l; dexamethasone and ibuprofen.

10. A process according to claim 1, in which the first solvent is an aprotic solvent, dimethyl sulfoxide (DMSO), 1-methyl-2-pyrrolidinone (NMP), dimethyl formamide (DMF) and dioxane.

11. A process according to claim 3, in which the polymer matrix is formed from a polyvinyl alcohol macromer, having more than one ethylenically unsaturated pendant group per molecule, by radical polymerisation of the ethylenic groups.

12. A process according to claim 11, in which the macromer is copolymerised with ethylenically unsaturated monomers.

13. A process according to claim 1, in which the particles used in step a) have a mean particle size in the range 50 to 1500 μm, when fully swollen with PBS at room temperature.

14. A process according to claim 10 in which the first solvent is selected from the group consisting of dimethyl sulfoxide (DMSO), 1-methyl-2-pyrrolidinone (NMP), dimethyl formamide (DMF) and dioxane.

15. A process according to claim 1 in which the water insoluble polymer is a polyvinyl alcohol.

16. A process according to claim 15 in which the water insoluble polymer is a covalently cross-linked polyvinyl alcohol.

17. A process according to claim 12 in which the ethylenically-unsaturated monomer is selected from non-ionic monomers, and ionic monomers and mixtures thereof.

18. A process according to claim 12 in which the monomers include anionic monomers.

19. A process according to claim 13 in which the mean particle size is in the range 50 to 1500 μm.

* * * * *